United States Patent
Alper et al.

(10) Patent No.: US 6,906,096 B2
(45) Date of Patent: Jun. 14, 2005

(54) 4,7-DISUBSTITUTED INDOLES AND METHODS OF MAKING

(75) Inventors: Phil B. Alper, Poway, CA (US); Khanh Linh T. Nguyen, Oceanside, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 10/608,949

(22) Filed: Jun. 26, 2003

(65) Prior Publication Data

US 2004/0110944 A1 Jun. 10, 2004

Related U.S. Application Data

(60) Provisional application No. 60/392,804, filed on Jun. 28, 2002.

(51) Int. Cl.$^7$ .................. A61K 31/404; C07D 209/04
(52) U.S. Cl. ................. 514/419; 548/452; 548/469; 548/491
(58) Field of Search ................ 548/452, 469, 548/491; 514/415, 419

(56) References Cited

U.S. PATENT DOCUMENTS

| | | | | |
|---|---|---|---|---|
| 4,238,486 A | * | 12/1980 | Jones | 514/229.5 |
| 5,486,525 A | * | 1/1996 | Summers et al. | 514/303 |
| 6,040,331 A | * | 3/2000 | Yamamoto et al. | 514/411 |

FOREIGN PATENT DOCUMENTS

WO   WO 2004/014294 A2   2/2004

OTHER PUBLICATIONS

Alper, P. et al., "Practical synthesis and elaboration of methyl 7–chloroindole–4–carboxylate" J. Org. Chem. 68(5):2051–2053 (2003) & Database HCAPLUS on STN, No. 2003:98290 Abstracts.

* cited by examiner

*Primary Examiner*—Golam M M Shameem
(74) *Attorney, Agent, or Firm*—Townsend and Townsend and Crew LLP

(57) ABSTRACT

The present invention provides, compounds, methods and compositions of biologically important indoles. In addition, the present invention provides synthesis methods for substituting leaving groups at positions 4 and 7 of the indole ring as diversity generating elements.

17 Claims, 1 Drawing Sheet

LSD (10)  Hippadine (12)  (-)-7-Octylindolactam V (15)

4,7-DISUBSTITUTED INDOLES AND METHODS OF MAKING

CROSS-REFERENCE TO RELATED APPLICATIONS

This application claims priority to U.S. Provisional Application No. 60/392,804 filed Jun. 28, 2002, which is incorporated herein by reference in its entirety for all purposes.

BACKGROUND OF THE INVENTION

Combinatorial chemistry has become a powerful tool for drug discovery in the pharmaceutical and biotechnology industries. Generally speaking, combinatorial chemistry is defined as the repetitive and systematic covalent attachment of different structural moieties to one another to produce a mixture of numerous distinct molecular entities or target molecules (i.e., combinatorial libraries). Desired target molecules include for example, peptides, oligonucleotides, and small organic molecules. Frequently, combinatorial chemistry is utilized to generate a group of structurally related analogs, which can then be evaluated to establish structure-activity relationships (SAR) and to optimize biological efficacy.

The prominence of the indole nucleus in medicinally important natural products and synthetic pharmaceuticals can hardly be overstated. (see, Gribble, in *Comprehensive Heterocyclic Chemistry II*, 2:207 (1996); Ban, et al., *N. Med. Res. Rev.*, 8(2):231 (1998); Saxton, *The Chemistry of Heterocyclic Compounds;* Wiley; New York, Vol. 25, Part IV (1983).) As a result, the chemistry of the substituted indole has received an enormous amount of attention. (see, Gribble, G. W. *J. Chem. Soc. Perkin Trans.* 1, 1045 (2000); Sundberg, in *Comprehensive Heterocyclic Chemistry II*, 2:119 (1996); Hughes, *Org. Prep. Proc. Int.*, 607 (1993)) The revolution of combinatorial chemistry of small molecules (see, Gordon, et al., *J. Med. Chem.*, 37(10):1385 (1994); Thompson, et al., *Chem. Rev.*, 96:555 (1996); Balkenhohl, et al., *Angew. Chem. Int. Ed. Enlg.*, 35:2288 (1996)) assured that the synthesis of indole containing lead compounds would be accelerated in a similar manner to all other scaffolds. (see, Hutchins, et al., *Tetrahedron Lett.*, 37(28):4869 (1996); Yun, et al., *Tetrahedron Lett.*, 37(40):7189 (1996); Hughes, *Tetrahedron Lett.*, 37(42):7595 (1996); Cheng, et al., *Tetrahedron Lett.*, 38(9):1497 (1997); Fagnola, et al., *Tetrahedron Lett.*, 38(13):2307 (1997); Zhang, et al., *J. Org. Chem.*, 62:1804 (1997); Arumugam, et al., *Tetrahedron Lett.*, 38(36): 6473 (1997); Collini, et al., *Tetrahedron Lett.*, 38(46):7963 (1997); Fokas, et al., *Tetrahedron Lett.*, 39:2235 (1998); Zhang, et al., *Tetrahedron Lett.*, 39:4449 (1998); Smith, et al., *Tetrahedron Lett.*, 39:8317 (1998); Wang, Y. et al., *Tetrahedron Lett.*, 39:9605 (1998); Stephensen, et al., *Tetrahedron Lett.*, 40:5799 (1999); Wang, et al., *Org. Lett.*, 1(10):1647 (1999); Zhang, et al., *Org. Lett.*, 2(1):89 (2000); Kraxner, et al., Synlett, (1): 125 (2000); Tois, et al., *Tetrahedron Lett.*, 41:2443 (2000); Ketcha, et al., *Tetrahedron Lett.*, 41:6253 (2000); Smith, et al., *Bioorg. Med. Chem. Lett.*, 10:2693 (2000); Stevenson, et al., *Bioorg. Med. Chem. Lett.*, 10:2697 (2000); Nettekoven, *Tetrahedron Lett.*, 41:8251 (2000); Meseguer, et al., *Chem. Eur. J.*, 6(21):3943 (2001); Cooper, et al., *Bioorg. Med. Chem. Lett.*, 11:1233 (2001).)

Biologically important indoles have a variety of activities and are useful for a number of indications. For example, lysergic acid diethyl amide has an indole core and is a hallucinogen and CNS activator (see, Jenner, et al., *Br. J. Pharmocol.*, 80, Suppl. 667P (1983); Kaiser, et al., *Med. Res. Rev.*, 5:145 (1985)). This indole also has a plethora of physiological effects (see, Bowers, et al., *Biochem. Pharmocol.*, 31:4093 (1982); Mornex, et al., *J. Pharmocol.*, 14 (Suppl. 3), 81 (1983)). Hippadine, another indole containing core molecule, causes reversible inhibition of fertility in male rats without anti-mitotic activity (see, Bowers, et al., *Biochem. Pharmocol.*, 31:4093 (1982); Mornex, et al., *J. Pharmocol.*, 14 (Suppl. 3), 81 (1983)). Moreover, (–)-7-octylindolactam V is a protein kinase C modulator and it too has an indole core (see, Kazanietz et al., *Mol. Pharmacol.*, 44:298 (1993)). The structural properties that these molecules share is their substitution at the 4 and 7 positions of the indole nucleus.

The tremendous variety of biological activities associated with indoles makes the indole nucleus very important biologically. What is needed in the art are new indoles having a variety of substituents at the 4 and 7 positions of the indole ring. The present invention satisfies this and other needs.

SUMMARY OF THE INVENTION

The present invention provides, compounds, compositions and methods of making biologically important indoles. In addition, the present invention provides synthesis methods for substituting leaving groups at positions 4 and 7 of the indole ring as diversity generating elements.

As such, in one aspect, the present invention provides a compound having Formula I:

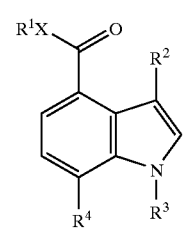

In Formula I, $R^1$ is a functional group including, but not limited to, hydrogen, optionally substituted alkyl, optionally substituted cycloalkyl, optionally substituted aryl, and optionally substituted heteroaryl.

$R^2$, in Formula I, is a functional group including, but not limited to, hydrogen, halogen, optionally substituted alkylamino, and C(O)—$R^5$, wherein $R^5$ is a member selected from the group of optionally substituted alkyl, optionally substituted cycloalkyl, optionally substituted aryl, and optionally substituted heteroaryl.

$R^3$, in Formula I, is a functional group including, but not limited to, hydrogen, and optionally substituted alkyl.

$R^4$, in Formula I, is a functional group including, but not limited to, halogen, optionally substituted alkyl, optionally substituted alkenyl, optionally substituted cycloalkyl, optionally substituted aryl, optionally substituted heteroaryl, and $S(O)_n$—$R^6$, wherein $R^6$ is a member selected from the group of optionally substituted alkyl, optionally substituted cycloalkyl, optionally substituted aryl, and optionally substituted heteroaryl, wherein n is an integer including 1, 2 or 3.

X, in Formula I, is a functional group including, but not limited to, a heteroatom such as O and NR, wherein R is hydrogen or optionally substituted alkyl. In an alternative embodiment, R and $R^2$ together with the atoms to which they are attached, join to form an optionally substituted 5-, 6- or 7-membered heterocyclic ring.

Certain compound of Formula I are preferred. For example, in one embodiment, preferred compounds have Formula Ia:

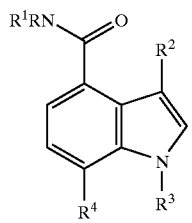

Ia

In Formula Ia, R is a functional group including, but not limited to, hydrogen and optionally substituted alkyl.

$R^1$ is a functional group including, but not limited to, hydrogen, optionally substituted alkyl, optionally substituted cycloalkyl, optionally substituted aryl, and optionally substituted heteroaryl.

$R^2$ is a functional group including, but not limited to, hydrogen, halogen, optionally substituted alkylamino, and C(O)—$R^5$, wherein $R^5$ is a member selected from the group consisting of optionally substituted alkyl, optionally substituted cycloalkyl, optionally substituted aryl, and optionally substituted heteroaryl.

$R^3$ is a functional group including, but not limited to, hydrogen, and optionally substituted alkyl.

$R^4$ is a functional group including, but not limited to, halogen, optionally substituted alkyl, optionally substituted alkenyl, optionally substituted cycloalkyl, optionally substituted aryl, optionally substituted heteroaryl, and S(O)$_n$—$R^6$, wherein $R^6$ is a member selected from the group of optionally substituted alkyl, optionally substituted cycloalkyl, optionally substituted aryl, and optionally substituted heteroaryl, wherein n is 1, 2 or 3.

In another preferred embodiment, the present invention provides compounds having Formula Ib:

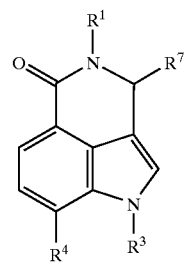

Ib

In Formula Ib, $R^1$ is a functional group including, but not limited to, hydrogen, optionally substituted alkyl, optionally substituted cycloalkyl, optionally substituted aryl, and optionally substituted heteroaryl.

$R^3$ is a functional group including, but not limited to, hydrogen, and optionally substituted alkyl.

$R^4$ is a functional group including, but not limited to, halogen, optionally substituted alkyl, optionally substituted alkenyl, optionally substituted cycloalkyl, optionally substituted aryl, optionally substituted heteroaryl, and S(O)$_n$—$R^6$, wherein R is a member selected from the group of optionally substituted alkyl, optionally substituted cycloalkyl, optionally substituted aryl, and optionally substituted heteroaryl, wherein n is 1, 2 or 3.

$R^7$ is a functional group including, but not limited to, hydrogen, optionally substituted alkyl, optionally substituted cycloalkyl, optionally substituted aryl, and optionally substituted heteroaryl. In especially preferred embodiments of Formula Ib, $R^7$ is hydrogen and $R^1$ is optionally substituted alkyl.

In another preferred embodiment, the present invention provides a compound having Formula Ic:

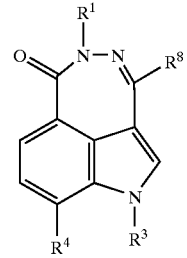

Ic

In Formula Ic, $R^1$ is a functional group including, but not limited to, hydrogen, optionally substituted alkyl, optionally substituted cycloalkyl, optionally substituted aryl, optionally substituted hydrazino, and optionally substituted heteroaryl.

$R^3$ is a functional group including, but not limited to, hydrogen, and optionally substituted alkyl.

$R^4$ is a functional group including, but not limited to, halogen, optionally substituted alkyl, optionally substituted alkenyl, optionally substituted cycloalkyl, optionally substituted aryl, optionally substituted heteroaryl, and S(O)$_n$—$R^6$, wherein $R^6$ is a member selected from the group of optionally substituted alkyl, optionally substituted cycloalkyl, optionally substituted aryl, and optionally substituted heteroaryl, wherein n is 1, 2 or 3.

$R^8$ is a functional group including, but not limited to, hydrogen, optionally substituted alkyl, optionally substituted cycloalkyl, optionally substituted aryl, and optionally substituted heteroaryl. In especially preferred embodiments of Formula Ic, $R^1$ and $R^8$ are both hydrogen.

In still yet another embodiment, the present invention provides a compound having Formula Id:

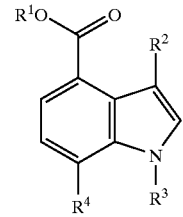

Id

In Formula Id, $R^1$ is a functional group including, but not limited to, hydrogen, optionally substituted alkyl, optionally substituted cycloalkyl, optionally substituted aryl, and optionally substituted heteroaryl.

$R^2$ is a functional group including, but not limited to, hydrogen, halogen, and C(O)—$R^5$, wherein $R^5$ is a member selected from the group consisting of optionally substituted alkyl, optionally substituted cycloalkyl, optionally substituted aryl, and optionally substituted heteroaryl.

$R^3$ is a functional group including, but not limited to, hydrogen, and optionally substituted alkyl.

$R^4$ is a functional group including, but not limited to, halogen, optionally substituted alkyl, optionally substituted alkenyl, optionally substituted cycloalkyl, optionally substi tuted aryl, optionally substituted heteroaryl, and S(O)$_n$—R$^6$, wherein R$^6$ is a member selected from the group of optionally substituted alkyl, optionally substituted cycloalkyl, optionally substituted aryl, and optionally substituted heteroaryl, wherein n is 1, 2 or 3.

In another embodiment, the present invention provides a compound having Formula Ie:

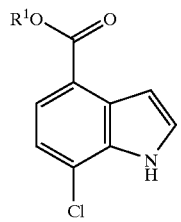

Ie

In Formula Ie, R$^1$ is a functional group including, but not limited to, methyl, ethyl, propyl and butyl, wherein methyl is especially preferred.

In still yet another embodiment, the present invention provides a method of making a compound having Formula II:

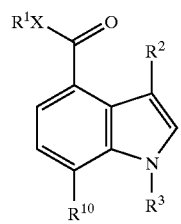

II

In Formula II, R$^1$, is a functional group including, but not limited to, hydrogen, optionally substituted alkyl, optionally substituted cycloalkyl, optionally substituted aryl, and optionally substituted heteroaryl.

R$^2$ is a functional group including, but not limited to, hydrogen, halogen, optionally substituted alkylamino, and C(O)—R$^5$, wherein R$^5$ is a member selected from the group consisting of optionally substituted alkyl, optionally substituted cycloalkyl, optionally substituted aryl, and optionally substituted heteroaryl.

R$^3$ is a functional group including, but not limited to, hydrogen, and optionally substituted alkyl.

R$^{10}$ is a functional group including, but not limited to, halogen, and S(O)$_n$—R$^6$, wherein R$^6$ is a member selected from the group consisting of optionally substituted alkyl, optionally substituted cycloalkyl, optionally substituted aryl, and optionally substituted heteroaryl, wherein n is 1, 2 or 3.

X is a heteroatom including, but not limited to, O and NR, wherein R is a member selected from the group of hydrogen and optionally substituted alkyl, or, alternatively, R and R$^2$ together with the atoms to which they are attached, join to form an optionally substituted 5-, 6- or 7-membered heterocyclic ring, the method comprising:

reacting a compound having Formula IIa:

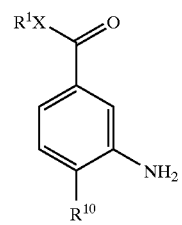

IIa with a sulfide to form a compound having a sulfide functionality having Formula IIb:

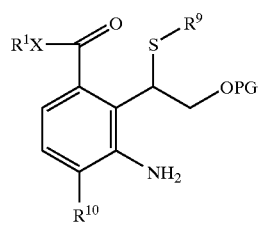

IIb wherein R$^9$ is a functional group including, but not limited to, optionally substituted alkyl, optionally substituted cycloalkyl, optionally substituted aryl, and optionally substituted heteroaryl and PG is a protective group;

cleaving the protecting group (PG) to form a compound having Formula IIc:

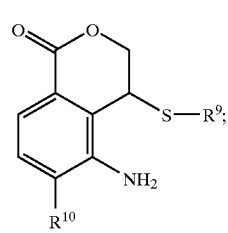

IIc protecting the primary amine to form a protected amine; and eliminating the sulfide functional group and subsequent alcoholysis to generate a compound of Formula II. The primary amine can be protected with for example, trifluoroacetic anhydride.

In still yet another embodiment, the present invention provides a method for generating a pharmacophore scaffold by introducing leaving groups at positions 4 and 7 of an indole ring, the method comprising:

reacting a compound having Formula IIIa:

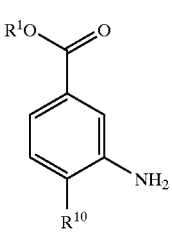

IIIa with a sulfide to form a compound having a sulfide functionality having Formula IIIb:

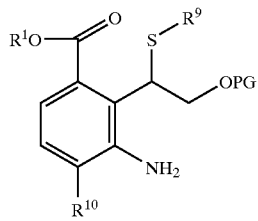

IIIb wherein $R^9$ is a is a functional group including, but not limited to, optionally substituted alkyl, optionally substituted cycloalkyl, optionally substituted aryl, and optionally substituted heteroaryl and PG is a protective group;

cleaving the protecting group (PG) to form a compound having Formula IIIc:

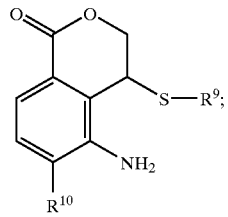

IIIc protecting the primary amine to form a protected amine; and eliminating the sulfide functional group and subsequent alcoholysis to generate a pharmacophore scaffold with leaving groups at positions 4 and 7 of the indole ring to generate a compound having Formula III:

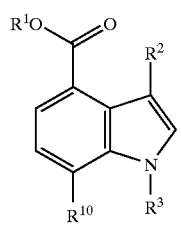

III

In Formula III, $R^1$ is a functional group including, but not limited to, optionally substituted alkyl, optionally substituted cycloalkyl, optionally substituted aryl, and optionally substituted heteroaryl.

$R^2$ is a functional group including, but not limited to, hydrogen, halogen, and C(O)—$R^5$, wherein $R^5$ is a member selected from the group of optionally substituted alkyl, optionally substituted cycloalkyl, optionally substituted aryl, and optionally substituted heteroaryl.

$R^3$ is a functional group including, but not limited to, hydrogen, and optionally substituted alkyl.

$R^{10}$ is a functional group including, but not limited to, halogen, and S(O)$_n$—$R^6$, wherein $R^6$ is a member selected from the group consisting of optionally substituted alkyl, optionally substituted cycloalkyl, optionally substituted aryl, and optionally substituted heteroaryl, wherein n is 1, 2 or 3.

In another embodiment, the present invention provides a method for making a compound having Formula IV:

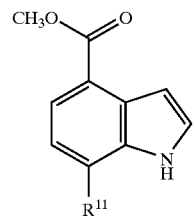

IV

In Formula IV, $R^{11}$ is a functional group including, but not limited to, optionally substituted alkenyl, optionally substituted aryl, and optionally substituted heteroaryl, the method comprising:

reacting a compound having Formula IVa:

IVa with an sp$^2$-sp$^2$ C—C bond coupling group in the presence of a catalyst such as Pd, to generate a compound of Formula IV. A preferred sp$^2$-sp$^2$ C—C bond coupling group is an aryl boronic acid moiety.

These and other features, advantages and embodiments, will become more apparent when read with the accompanying drawings and detailed description that follow.

DETAILED DESCRIPTION OF THE INVENTION AND PREFERRED EMBODIMENTS

I. Definitions

As used herein, the term "alkyl" denotes branched or unbranched hydrocarbon chains, preferably having about 1 to about 24 carbons. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkenyl" denotes branched or unbranched hydrocarbon chains containing one or more carbon-carbon double bonds, preferably having about 8 to about 24 carbons.

The term "cycloalkyl" by themselves or in combination with other terms represents cyclic versions of "alkyl" respectively. The term "cycloalkyl" is meant to include bicyclic, tricyclic and polycyclic versions thereof. Examples of cycloalkyl include cyclopentyl, cyclohexyl, 1-cyclohexenyl, 3-cyclohexenyl, cycloheptyl, bicyclo[2.2.1]heptyl, bicyclo[2.2.2]octyl, adamantyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. Non-limiting examples of aryl groups include phenyl, 1-naphthyl, 2-naphthyl, 4-biphenyl, and the like. Substituents for each of the above noted aryl ring systems are selected from the group of acceptable substituents described below.

The term "heteroaryl" means an aromatic substituent which can be a single ring or multiple rings having from 1, 2, 3 or 4 heteroatoms selected from N, O, and S, wherein the nitrogen and sulfur atoms are optionally oxidized, and the nitrogen atom(s) are optionally quaternized. The heteroaryl groups can be attached to the remainder of the molecule through a carbon atom or a heteroatom. Non-limiting examples of aryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

II. General

Figure 1:
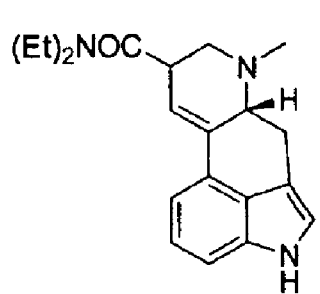
FIG. 1 illustrates compounds having an indole core with a variety of biological activities.
Figure 1:
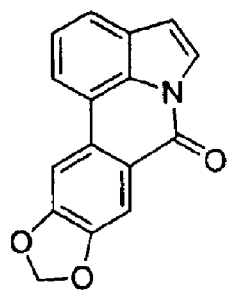
Figure 1:
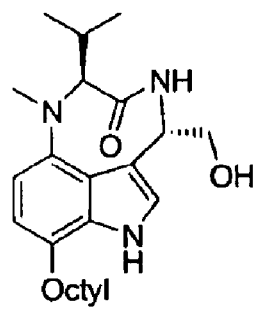

FIG. 1 sets forth three natural products having indole rings as a core. The compounds set forth therein have a variety of biological activities. For example, lysergic acid diethyl amide 10 is a hallucinogen and CNS activator. Hippadine 12 causes reversible inhibition of fertility in male rats without anti-mitotic activity. In addition, (−)-7-octylindolactam V 15 is a protein kinase C modulator.

The compounds and compositions of the present invention have a variety of biological activities including for example, CNS activation, reversible inhibition of fertility in rats, and protein kinase C modulation.

III. Compounds

In certain aspects, the present invention provides compounds and compositions useful in a variety of biological indications. In one embodiment, the present invention provides a compound of Formula I:

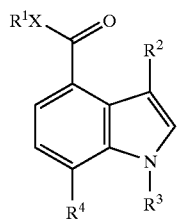

I wherein: $R^1$, $R^2$, $R^3$, $R^4$ and X have previously been defined. In certain preferred instances, the compounds of Formula I have Formula Ia:

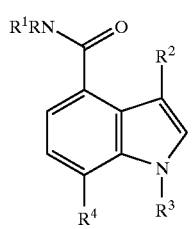

Ia wherein R is hydrogen or optionally substituted alkyl, and $R^1$, $R^2$, $R^3$ and $R^4$ have been defined as in Formula I.

In another embodiment, the compounds of Formula I have Formula Ib:

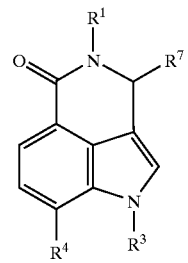

Ib wherein: $R^1$, $R^3$ and $R^4$ have been defined as in for Formula I. In Formula Ib, $R^7$ is a functional group such as hydrogen, optionally substituted alkyl, optionally substituted cycloalkyl, optionally substituted aryl, and optionally substituted heteroaryl. In one preferred aspect, $R^1$ is hydrogen and $R^7$ is optionally substituted alkyl group, such a methyl, ethyl, propyl, butyl and the like.

In another embodiment, the compounds of Formula I have Formula Ic:

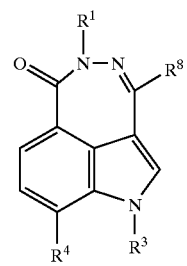

Ic wherein: $R^1$, $R^3$, $R^4$ have been defined as in for Formula I. $R^8$ is hydrogen, optionally substituted alkyl, optionally substituted cycloalkyl, optionally substituted aryl, and optionally substituted heteroaryl. In one preferred aspect, $R^1$ and $R^8$ are both hydrogen.

In another embodiment, the compounds of Formula I have Formula Id:

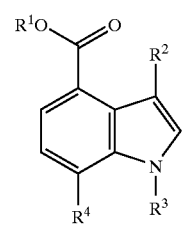

Id wherein $R^1$, $R^2$, $R^3$ and $R^4$ have been defined as in Formula I.

In another embodiment, the compound of Formula I has Formula Ie:

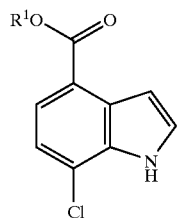

Ie wherein $R^1$ has been defined as in Formula I. Preferably, $R^1$ is methyl, ethyl, propyl and butyl, more preferably, $R^1$ is methyl.

IV. Methods

In one embodiment, the present invention provides methods for generating substituted indoles having substituents at the 4 and 7 positions of the indole ring. In certain aspects, using the multistep synthesis procedure of the present invention, an indole scaffold can be generated in good yield from commercially available starting materials. Advantageously, the synthesis methods of the present invention are robust and scalable. In certain instances, a halide on the 4 position can be readily substituted using for example, palladium chemistry herein described.

Scheme 1 below illustrates starting material that can be used to generate compounds of the present invention.

Scheme 1

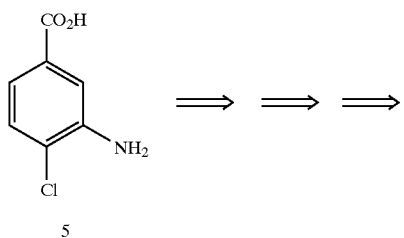

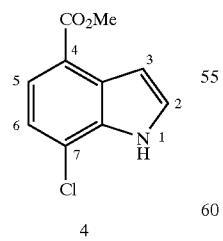

4

As shown in Scheme 1, positions 4 and 7 of compound 4 are substituted with good leaving groups to generate an indole pharmacophore scaffold.

In certain aspects, the present invention provides a method of making a compound of Formula II:

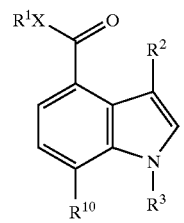

II wherein: $R^1$, $R^2$, $R^3$, and $R^{10}$ have previously been described.

In one embodiment, the method comprises reacting a compound of Formula IIa:

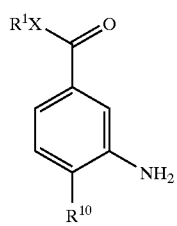

IIa wherein: $R^1$, $R^{10}$ and X have previously been defined, with a sulfide functionality. Various sulfides can be use in the present methods. As used herein, sulfides include for example, alkylthio and arylthio functional groups. In one preferred embodiment, the sulfide suitable for use in the present methods is a sulfide having Formula IId:

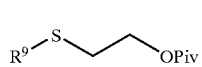

IId wherein $R^9$ is for example, an optionally substituted alkyl or optionally substituted aryl group. In certain aspects, the sulfide functional group is activated using for example, sulfuryl chloride. Preferably, the sulfide functional group is coupled to a compound of Formula IIa at low temperature in the presence of a hindered base, such as collidine. Those of skill in the art will know of other hindered bases suitable for use in the present methods.

Reacting the sulfide functional group with a compound of Formula IIa will generate a compound of Formula IIb:

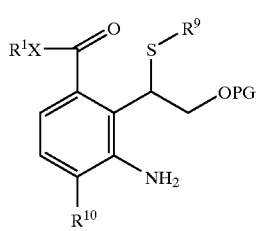

IIb wherein PG is a protecting group. Suitable protecting groups include esters such as acetate esters, pivalate esters, benzoate esters and the like. Bulky esters such as a pivalate ester, are preferred.

Thereafter, the protecting group (PG) is cleaved to form a compound having Formula IIc:

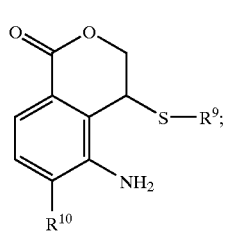

IIc the primary amine is protected to form a protected amine; and thereafter, the sulfide functional group is eliminated, with subsequent alcoholysis to generate a compound of Formula II.

In an illustrative embodiment, not in any way intended to be limiting, Scheme II sets forth an example of the present method. One of ordinary skill in the art will recognize many other variations, alternatives, and modifications.

In this example, sulfide 6, which is available in high yields from 2-methylthioethanol, is coupled with methyl-3-chloro-4-amnobenzoate (7) (available on large scale in high yield from 5) to form a sulfilimine (Scheme 2). Activation of 6 using for example, $SO_2Cl_2$, generates an electrophilic species which couples with 7. The reaction is preferably run at low temperature in the presence of a hindered base. The resulting sulfilimine is then treated with for example, triethylamine and heated to generate, after aqueous workup, a rearrangement product 8. In certain aspects, the sulfilimine is heated to about 40° C. to about 100° C., more preferably about 50° C. to about 80° C.

Scheme 2

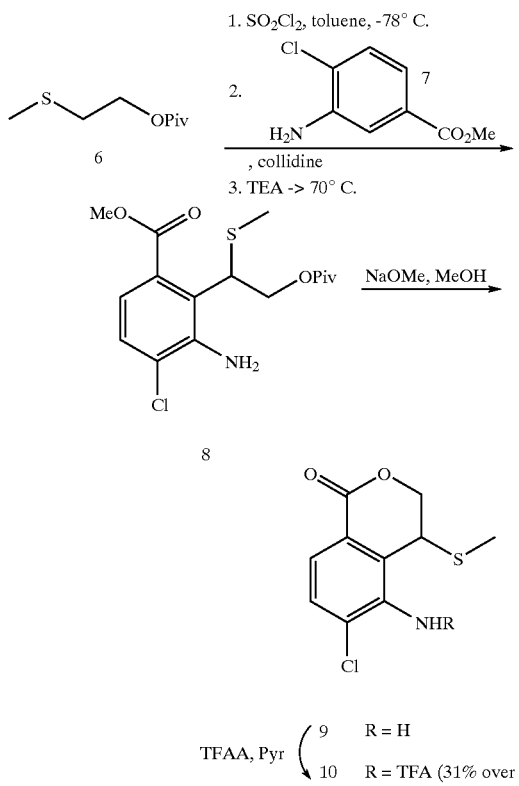

Treatment of 8 with for example, NaOMe in MeOH, will effectuate the cleavage of the pivalate ester and subsequent spontaneous cyclization to the lactone (9). The lactone 9 is treated with TFAA and pyridine, which results in trifluoroacetamide 10. Isolation of 10 is via crystallization.

Scheme 3

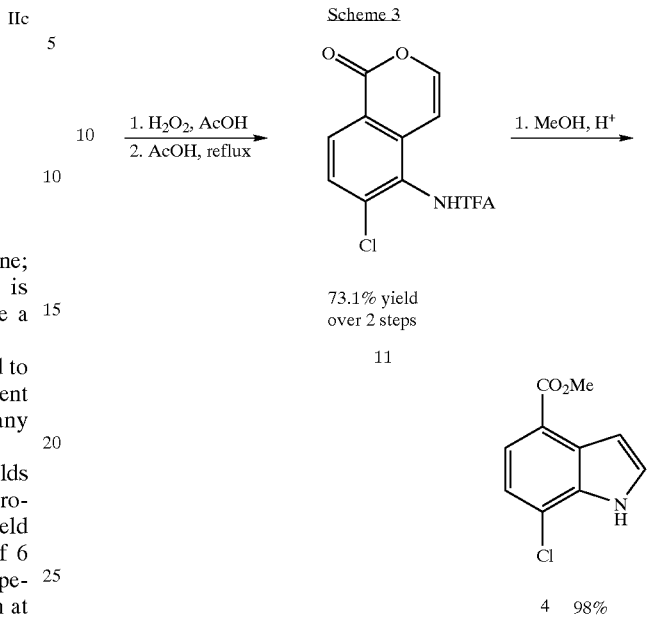

To generate 4 from 10, the sulfide is eliminated to generate a double bond. This can be accomplished, by for example, oxidizing the sulfide to the sulfoxides with an oxidizing agent such as hydrogen peroxide (e.g., using a stoichiometric amount), and eliminating methyl sulfinic acid by for example, refluxing in a weak acid (e.g., AcOH) to generate the isocoumarin 11 as a solid (see, Scheme 3).

Treatment of 11 with a mineral acid (e.g., sulfuric acid) in refluxing alkanol (e.g., methanol) affords 4 as a pure substance in good yield after aqueous workup.

In still another embodiment, the present invention provides a method for making a compound having Formula IV:

IV wherein: $R^{11}$ has been defined.

The method comprises reacting a compound having Formula IVa:

IVa with an $sp^2$-$sp^2$ C—C bond coupling group in the presence of a Pd catalyst, to generate the compound of Formula IVa. A preferred $sp^2$-$sp^2$ C—C bond coupling group is an aryl boronic acid moiety, such as phenylboronic acid. Those of skill in the art will know of other aryl boronic acid moieties suitable for use in the present invention.

In the present methods, palladium catalyzed carbon-carbon bond forming chemistry can be used to couple a $sp^2$-$sp^2$ C—C bond at position 7 of an indole ring. In certain preferred embodiments, the method for making 7-substituted indoles is set forth in Scheme 4. This example is merely illustrative and is not intended to limit the invention.

Because it is known that the indole NH is reactive in palladium mediated reactions, $CsHCO_3$ or a similar reagent can be used to prevent such side reactions. The coupling chemistry is efficient. As the products can be purified by extraction into aqueous base, purification is facile.

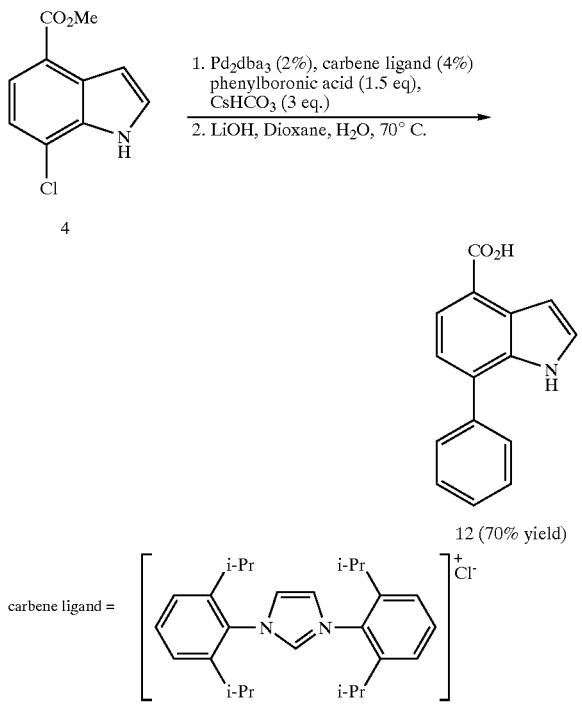

Scheme 4

Compound 12 can thereafter be modified at position 4. For example, amides can be made using a stoichiometric amount of the carboxylic acid, amine and solvent (e.g., DMAP in DMF) with 1.1 equivalents of a promoter (e.g., EDCI). Suitable amines include, but are not limited to, primary amines, secondary amines, alkylamines, arylamines, and heterocylic amines. The heterocyclic amines can be aromatic. Specific examples include, butylamine, phenylamine, dipropylamine and the like. The reactions can be run in parallel with multiwell plates. For example, the wells are charged with the parent indole acids and thereafter with amines.

V. Compositions and Doses

In certain aspects, the present invention provides compounds and compositions useful in a variety of biological indications. An effective quantity of the compound of interest is employed in various treatments. The dosage of compounds used in accordance with the invention varies depending on the compound and the condition being treated. The age, weight, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 100 to about 600 mg twice a day. More typically, a single dose is about 100–200 mg of compound given twice a day. A convenient oral dose for an adult patient is 200 mg twice a day. A dosage range for topical treatment is about 0.1% to about 10% (weight/volume) in a cream or ointment, applied twice a day. A usual dose for intra-articular injection is 20–40 mg injected per joint, not generally exceeding three joints per therapy session. A typical dosage for intra-dermal administration is about 20–75 mg per injection per site. A typical dosage for intravenous or intramuscular administration in an adult patient would be between 1 mg and 1000 mg per day given in single or divided doses depending on the judgment of the practitioner.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

In other aspects, the compounds of the present invention are given independently for uses specified herein, or are given as adjuvants, i.e., in combination with existing pharmacological therapeutic agent or agents or other pharmaceutical agent or agents yet to be discovered.

The foregoing is offered primarily for purposes of illustration. It will be readily apparent to those of ordinary skill in the art that the operating conditions, materials, procedural steps and other parameters of the system described herein may be further modified or substituted in various ways without departing from the spirit and scope of the invention. For example, the invention has been described with human patients as the usual recipient, but veterinary use is also contemplated.

VI. Experimental Section

A. General Experimental Details

Unless otherwise stated glassware was air dried prior to use with no special precautions taken for drying. All solvents stated as anhydrous were purchased that way from the manufacturer and used as received. All other purchased reagents were used as received. Unless otherwise stated, all reactions were carried out under a positive pressure of nitrogen. NMR spectra were taken on a Bruker DPX-400 instrument and the data were reported as follows: chemical shift on the d scale (using residual protio solvent as the internal standard), multiplicity (s=singlet, d=doublet, t=triplet, q=quartet, m=multiplet), integration and coupling constant in hertz. $^{13}C$ spectra were recorded as APT experiments on a Bruker DPX-400 (100 MHz) instrument and were reported in ppm with residual solvent for internal standard. Melting points were obtained on a Thomas Hoover Uni-Melt apparatus. IR spectra were recorded on a Nicolet Avatar 380 FT-IR instrument.

2-Methylthioethyl pivalate (6). (U.S. Pat. No. 2,680,730, 1950, DuPont de Nemours and Co.) A 2 L flask was charged with methylthioethanol (100.93 g, 1.095 mol), methylene chloride (500 mL) and pyridine (95.3 g, 1.204 mol). The flask was then cooled in an ice/water bath. Pivaloyl chloride (139 g/1.150 mol) was then added slowly via pressure equalizing addition funnel (~1 hr). The reaction was stirred overnight and then quenched with MeOH (10 mL). After 30 min, the reaction was extracted with 3 200 mL portions of aqueous $^1$N HCl. The organics were dried over $MgSO_4$ and the solvent was removed. After keeping the material at 15 mbar and 30° C. for 30 min on a rotary evaporator, the material was solvent free and yielded 186.9 g (96.8%) of an oil: $^1$H NMR ($CDCl_3$, 400 MHz) $\delta$1.22 (s, 9H), 2.17 (s, 3H), 2.73 (dd, 2H, $J_1=J_2=6.8$), 4.24 (dd, 2H, $J_1=J_2=6.8$); $^{13}$C NMR ($CDCl_3$, 100 MHz) $\delta$27.4, 32.8, 38.9, 63.2, 178.6; IR (neat) 2971.2, 2916.6, 2869.7, 1725.6; GC-MS calcd. for $C_8H_{16}O_2S$ (M+H$^+$) 176, found 176.

Methyl-3-amino-4-chlorobenzoate (7). A 5 liter, 3 neck roundbottom flask was charged with 3-amino-4-chlorobenzoic acid (5) (670 g, 3.905 mol). This material was then treated with MeOH (1340 mL) and trimethyl orthoformate (456 g, 4.295 mol). The flask was then equipped with mechanical stirring an efficient condenser with a drying tube (drierite) and a pressure equalizing addition funnel. The reaction was then heated to 60° C. and sulfuric acid (421 g, 4.295 mol) was added at such a rate as to keep the reflux from being too vigorous. It is essential to maintain good stirring during this operation. After the addition was complete, the reaction was refluxed until all the solid dissolved (~2 h). The MeOH was then distilled with the pot temperature at 80° C. until a solid came out of solution. The heating bath was removed and 1.2 L of EtOAc was added to the reaction. After standing overnight, the resulting solid was collected. The mother liquors were evaporated until the total volume was less than 1 L and a copious amount of solid had come out. This material was also collected by filtration and the 2 batches were combined in a 5 L flask. The material was treated with 1 L each of water and EtOAc. After all the material dissolved, the reaction was treated with 200 g of NaOH in portions. The organic layer was collected and washed twice with 500 mL portions of 1 M aqueous NaOH, dried over $Na_2SO_4$ and the solvent was removed. The resulting solid was dried under high vacuum overnight to yield 580 g (80.0%) of solid: $^1$H NMR ($CDCl_3$, 400 MHz) $\delta$3.90 (s, 3H), 4.25 (broad s, 1H), 7.31 (d, 1H, J=8.3), 7.36 (dd, 1H, $J_1=8.3$, $J_2=1.9$), 7.46 (d, 1H, J=1.9); $^{13}$C NMR ($CDCl_3$, 100 MHz) $\delta$52.4, 116.8, 120.1, 124.1, 129.6, 129.8, 143.1; IR (neat) 3468.7, 3360.8, 1710.9, 1626.2; HRMS calcd. for $C_8H_8ClNO_2$ (M+H$^+$) 186.0316, found 186.0312.

Compound 10. A 3-neck 3 L roundbottom flask was equipped with mechanical stirring and was charged with 2-methylthioethyl pivalate (6) (52.2 g, 296 mmol) and dry toluene (1.5 L). The flask was cooled in a dry ice/acetone bath (internal temperature of −60° C.) and sulfuryl chloride (38.2 g, 283 mmol) was added dropwise to the reaction via cannula. The reaction was stirred cold for 2 h. A solution of methyl-3-amino-4-chlorobenzoate (7) (50 g, 269 mmol) in collidine (65.2 g, 538 mmol) was then added over 45 minutes into the stirring cooled solution of activated sulfide. The reaction became homogenous during the addition. The cooling was discontinued and the reaction was allowed warm up. Triethylamine (43.6 g, 431 mmol) was added when the internal temperature of the reaction reached 0° C. and a voluminous precipitate was observed. The reaction was heated to 70° C. overnight. After cooling, the reaction was extracted with 1 portion of water (500 mL), 2 portions of 6 N aqueous HCl (500 mL each) 2 portions of concentrated HCl (50 mL each), 2 portions of 1 M NaOH (500 mL each) and finally a mixture of saturated aqueous $NaHCO_3$ and saturated NaCl (250 mL each). The organics were dried over $MgSO_4$ and the solvent was removed. The residue was dissolved in dry MeOH (100 mL) and treated with a solution of 25% NaOMe in MeOH (12 mL). After stirring for 4 h, the reaction was quenched with acetic acid (8 mL) and the solvent was removed. The reaction was then partitioned between EtOAc and water and extracted with water again and then with aqueous 0.5 M $K_2HPO_4$ buffer. The organic phase was then dried over $MgSO_4$ and the solvent was removed. The residue was dissolved in methylene chloride (300 mL), treated with pyridine (23.3 g, 293 mmol) and cooled in an ice/water bath. Trifluoroacetic anhydride (49.2 g, 234 mmol) was added slowly via dropping funnel. After the addition was complete, the reaction was extracted with aqueous 1 M HCl (300 mL) and the organic phase was cooled in a refrigerator overnight. The resulting solid was collected in 2 crops and dried under high vacuum to yield 29.46 g (32.2%) m.p. 197–200: $^1$H NMR (DMSO, 400 MHz) $\delta$2.13 (s, 3H), 4.71 (dd, 1H, $J_1=12.2$, $J_2=1.2$), 4.76 (dd, 1H, $J_1=12.2$, $J_2=2.5$), 7.80 (d, 1H, J=8.5), 8.02 (d, 1H, J=8.5), 11.52 (s, 1H)); $^{13}$C NMR (DMSO, 100 MHz) $\delta$ 15.2, 38.8, 70.0, 115.3, 118.1, 125.6, 130.6, 130.9, 131.6, 138.9, 163.4; IR (neat) 3281.6, 1710.6; HRMS (MALDI-FTMS) calcd. for $C_{12}H_9ClF_3NO_3S$ (M+Na$^+$) 361.9836, found 361.9849.

Compound 11. A suspension of 10 (35 g, 103.0 mmol) in acetic acid (100 mL) was treated with an aqueous solution of titrated $H_2O_2$ (11.675 g of a 30.02% by weight solution, 103.0 mmol). The reaction was stirred overnight. The solvent was removed and the reaction was co evaporated once with acetic acid. The residue was dissolved in 200 mL of acetic acid and the reaction was evacuated and back filled with nitrogen 3 times. The solution was then refluxed for 3.5 h, cooled and the solvent was mostly removed (caution: stench). The residue was triturated with methylene chloride and cooled in a refrigerator overnight. Collection yielded 21.95 g (73.1%) of an off-white solid m.p. (215–218): $^1$H NMR (DMSO, 400 MHz) $\delta$6.69 (d, 1H, J=5.8), 7.69 (d, 1H, J=5.8), 7.84 (d, 1H, J=8.6), 8.21 (d, 1H, J=8.6), 11.69 (s, 1H); $^{13}$C NMR (DMSO, 100 MHz) $\delta$101.9, 114.4, 117.3, 120.7, 127.3, 129.7, 130.5, 135.6, 139.0, 147.9, 155.6, 155.9, 160.2; IR (neat) 3194.2, 3038.1, 1712.0; HRMS (MALDI-FTMS) calcd. for $C_{11}H_5ClF_3NO_3$ (M−H$^-$) 289.9837, found 289.9844.

4-Carbomethoxy-7-chloroindole (4). A suspension of 11 (21.95 g, 75.27 mmol) in MeOH (150 mL) was treated with $H_2SO_4$ (29.5 g, 301 mmol) and refluxed overnight. The reaction was cooled and the solvent was removed without warming up the bath. The residue was picked up in EtOAc and poured into a rapidly stirring solution of aqueous sodium hydroxide (30 g) in water (200 mL). The aqueous phase was extracted once more with EtOAc and the combined organics were dried over $MgSO_4$ and the solvent was removed to yield 15.5 g (98%) of 4 as a solid m.p. ( ): $^1$H NMR ($CDCl_3$, 400 MHz) $\delta$4.01 (s, 3H), 7.24–7.30 (m, 2H), 7.42 (dd, 1H, $J_1=J_2=2.6$), 7.88 (d, 1H, J=8.1), 8.61 (s, 1H); $^{13}$C NMR ($CDCl_3$, 100 MHz) $\delta$52.1, 105.5, 121.0, 122.0, 124.5, 127.0; IR (neat) 3290.4, 1679.7; HRMS calcd. for $C_{10}H_8ClNO_2$ (M+H$^+$) 210.0316, found 210.0316.

The following is a representative procedure for the functionalization of 1 using a boronic acid reagent: A 100 mL roundbottom flask was equipped with a 3-way stopcock and a magnetic stir bar and flame dried under vacuum. The flask was then back-filled with nitrogen and charged with 4-carbomethoxy-7-chloroindole (4) (2 g, 9.54 mmol), $Pd_2dba_3$ (109 mg, 119 $\mu$mol), carbene ligand (Huang, et al., *J. Am. Chem. Soc.*, 9889–90 (1999)) (203 mg, 477 $\mu$mol), aryl- or vinylboronic acid (2.32 g, 14.3 mmol), and CsHCO₃ prepared as described above (5.55 g, 28.6 mmol). The flask was then evacuated and back filled with nitrogen again and charged with 1,4-dioxane (20 mL) under positive nitrogen pressure. The flask was then sealed and dipped into a pre-heated 80° C. bath. After stirring at this temperature overnight, the solvent was removed and the reaction was partitioned between EtOAc and a mixture of water and brine (1:1). The organics were extracted once more with a similar mixture (if desired, the reaction mass may be filtered through a plug of celite to help in the workup). The organics were dried over MgSO₄ and the solvent was removed. The residue was passed through a short silica gel plug eluting with EtOAc to remove Pd impurities and the solvent was removed. The residue was dissolved in 1,4-dioxane (30 mL) and heated to 70° C. The reaction was then treated with a solution of LiOH (685 mg, 28.6 mmol) in water (10 mL). Some precipitate was observed. After stirring at the same temperature for 3 h, the reaction was cooled to room temperature and the solvent was removed. The reaction was partitioned between EtOAc (~40 mL) and 1 M aqueous NaOH (~40 mL). The organics were extracted 3 times more (~40 mL each) with base solution and discarded. The combined base extracts were acidified with concentrated HCl. The resulting solid was collected by filtration, washed thoroughly with water and then once with hexane. If the indole acid was not freely soluble in MeOH or diethyl ether, then the material was washed once with either one of these solvents. The resulting solid was collected and dried under high vacuum overnight.

The following is a representative procedure for the arylation of 1 using a tributylstannyl reagent: A 50 mL Schlenk flask was equipped with a magnetic stir bar and flame dried under vacuum. The flask was then back-filled with nitrogen and charged with 4-carbomethoxy-7-chloroindole (4) (2 g, 9.54 mmol) and Pd₂ dba₃ (349 mg, 0.38 mmol). The flask was then evacuated and back filled with nitrogen. The tributylstannyl reagent (11.2 mmol) was added along with 1,4-dioxane (20 mL) and a 0.5 M solution of P(t-Bu)₃ in 1,4-dioxane (3.04 mL, 1.52 mmol). The flask was then sealed and dipped into a pre-heated 120° C. bath. After stirring overnight, the reaction was approx. 90% complete. The reaction was applied to a silica gel plug and eluted with EtOAc. The solvent was removed and the reaction was crystallized from toluene (1.1 g). The mother liquors from the crystallization were eluted through a column using 10% EtOAc in dichloromethane and crystallized again from toluene to yield and additional gram of material. The combined solids were dissolved in 1,4-dioxane (30 mL) and heated to 70° C. The reaction was then treated with a solution of LiOH (635 mg, 28.6 mmol) in water (10 mL). After 3 h, the solvent was removed and the reaction was partitioned between EtOAc and water. The organics were extracted with 1 M aqueous NaOH 5 times and discarded. The combined aqueous extracts were acidified with concentrated HCl and the resulting solid was collected and dried under high vacuum to afford the title material.

12. m.p. (197–198); ¹H NMR (DMSO, 400 MHz) δ7.09 (dd, 1H, J₁=2.9, J₂=1.9), 7.21 (d, 1H, J=7.7), 7.45–7.52 (m, 2H), 7.54–7.59 (m, 2H), 7.66–7.71 (m, 2H), 7.82 (d, 1H, J=7.7), 11.24 (s, 1H), 12.58 (s, 1H); ¹³C NMR (DMSO, 100 MHz) δ102.9, 120.5, 123.0, 127.9, 128.2, 128.4, 129.0, 129.8, 133.8, 137.9, 168.3; IR (neat) 3451.6, 3428.2, 1662.3; HRMS (MALDI-FTMS) calcd. for $C_{15}H_{11}NO_2$ (M+H⁺) 238.0863, found 238.0861.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula

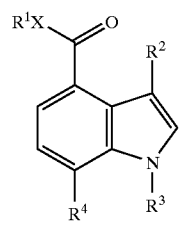

I wherein:
R¹ is a member selected from the group consisting of hydrogen, optionally substituted alkyl, optionally substituted cycloalkyl, optionally substituted aryl, and optionally substituted heteroaryl;
R² is a member selected from the group consisting of hydrogen, halogen, optionally substituted alkylamino, and C(O)—R⁵, wherein R⁵ is a member selected from the group consisting of optionally substituted alkyl, optionally substituted cycloalkyl, optionally substituted aryl, and optionally substituted heteroaryl;
R³ is a member selected from the group consisting of hydrogen, and optionally substituted alkyl;
R⁴ is a member selected from the group consisting of halogen, optionally substituted alkyl, optionally substituted alkenyl, optionally substituted cycloalkyl, optionally substituted aryl, optionally substituted heteroaryl, and S(O)ₙ—R⁶, wherein R⁶ is a member selected from the group consisting of optionally substituted alkyl, optionally substituted cycloalkyl, optionally substituted aryl, and optionally substituted heteroaryl, wherein n is 1, 2 or 3; and
X is a heteroatom selected from the group consisting of O and NR, wherein R is a member selected from the group consisting of hydrogen and optionally substituted alkyl, or, alternatively, R and R² together with the atoms to which they are attached, join to form an optionally substituted 5-, 6- or 7-membered heterocyclic ring.

2. The compound of claim 1, said compound having the formula:

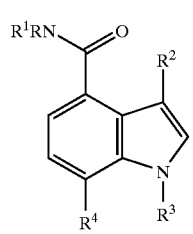

Ia wherein:
R is a member selected from the group consisting of hydrogen and optionally substituted alkyl;

$R^1$ is a member selected from the group consisting of hydrogen, optionally substituted alkyl, optionally substituted cycloalkyl, optionally substituted aryl, and optionally substituted heteroaryl;

$R^2$ is a member selected from the group consisting of hydrogen, halogen, optionally substituted alkylamino, and C(O)—$R^5$, wherein $R^5$ is a member selected from the group consisting of optionally substituted alkyl, optionally substituted cycloalkyl, optionally substituted aryl, and optionally substituted heteroaryl;

$R^3$ is a member selected from the group consisting of hydrogen, and optionally substituted alkyl; and $R^4$ is a member selected from the group consisting of halogen, optionally substituted alkyl, optionally substituted alkenyl, optionally substituted cycloalkyl, optionally substituted aryl, optionally substituted heteroaryl, and S(O)$_n$—$R^6$, wherein $R^6$ is a member selected from the group consisting of optionally substituted alkyl, optionally substituted cycloalkyl, optionally substituted aryl, and optionally substituted heteroaryl, wherein n is 1, 2 or 3.

3. The compound of claim 1, said compound having the formula:

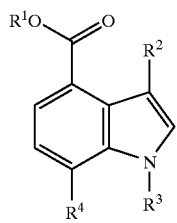

Id $R^1$ is a member selected from the group consisting of hydrogen, optionally substituted alkyl, optionally substituted cycloalkyl, optionally substituted aryl, and optionally substituted heteroaryl;

$R^2$ is a member selected from the group consisting of hydrogen, halogen, and C(O)—$R^5$, wherein $R^5$ is a member selected from the group consisting of optionally substutited alkyl, optionally substituted cycloalkyl, optionally substituted aryl, and optionally substituted heteroaryl;

$R^3$ is a member selected from the group consisting of hydrogen, and optionally substituted alkyl;

$R^4$ is a member selected from the group consisting of halogen, optionally substituted alkyl, optionally substituted alkenyl, optionally substituted cycloalkyl, optionally substituted aryl, optionally substituted heteroaryl, and S(O)$_n$—$R^6$, wherein $R^6$ is a member selected from the group consisting of optionally substituted alkyl, optionally substituted cycloalkyl, optionally substituted aryl, and optionally substituted heteroaryl, wherein n is 1, 2 or 3.

4. The compound of claim 3, wherein:

$R^1$ is a member selected from the group consisting of optionally substituted $C_1$–$C_6$ alkyl, and optionally substituted $C_5$–$C_6$ cycloalkyl;

$R^2$ is a hydrogen; and $R^4$ is halogen, the group consisting of halogen, and S(O)$_n$—$R^6$, wherein $R^6$ is an optionally substituted alkyl, wherein n is 1 or 2.

5. The compound of claim 4, wherein:

$R^1$ is $C_1$–$C_6$ alkyl;

$R^2$ is a hydrogen; and $R^4$ is a halogen, wherein n is 1 or 2.

6. The compound of claim 5, wherein:

$R^1$ is a member selected from the group consisting of methyl, ethyl, propyl and butyl.

7. The compound of claim 3, said compound having the formula:

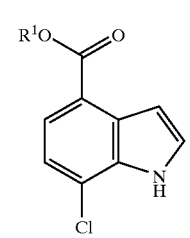

Ie wherein $R^1$ is a member selected from the group consisting of methyl, ethyl, propyl and butyl.

8. The compound of claim 7, wherein: $R^1$ is methyl.

9. A method of making a compound having the formula:

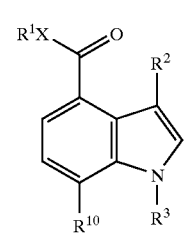

II wherein:

$R^1$ is a member selected from the group consisting of hydrogen, optionally substituted alkyl, optionally substituted cycloalkyl, optionally substituted aryl, and optionally substituted heteroaryl;

$R^2$ is a member selected from the group consisting of hydrogen, halogen, optionally substituted alkylamino, and C(O)—$R^5$, wherein $R^5$ is a member selected from the group consisting of optionally substituted alkyl, optionally substituted cycloalkyl, optionally substituted aryl, and optionally substituted heteroaryl;

$R^3$ is a member selected from the group consisting of hydrogen, and optionally substituted alkyl;

$R^{10}$ is a member selected from the group consisting of halogen, and S(O)$_n$—R wherein $R^6$ is a member selected from the group consisting of optionally substituted alkyl, optionally substituted cycloalkyl, optionally substituted aryl, and optionally substituted heteroaryl, wherein n is 1, 2 or 3; and X is a heteroatom selected from O and NR, wherein R is a member selected from the group consisting of hydrogen and optionally substituted alkyl, or, alternatively, R and $R^2$ together with the atoms to which they are attached, join to form an optionally substituted 5-, 6- or 7-membered heterocyclic ring, said method comprising:

reacting a compound having the formula:

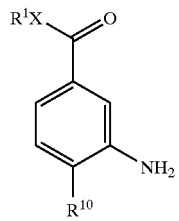

IIa with a sulfide to form a compound having a sulfide functionality of the formula

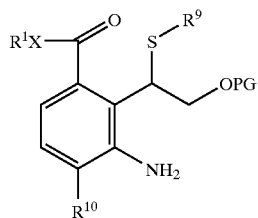

IIb wherein $R^9$ is a member selected from the group consisting of optionally substituted alkyl, optionally substituted cycloalkyl, optionally substituted aryl, and optionally substituted heteroaryl; and PG is a protective group;

cleaving said protecting group (PG) to form a compound having the formula:

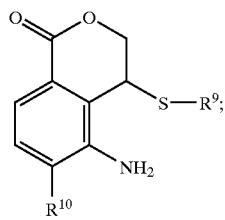

IIc protecting the primary amine to form a protected amine; and eliminating said sulfide functional group and subsequent alcoholysis to generate a compound of Formula II.

10. The method of claim 9, wherein said sulfide has the formula:

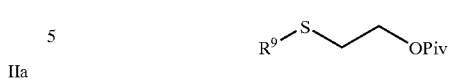

IId wherein said sulfide functional group is activated using $SO_2Cl_2$, and said sulfide functional group is coupled to a compound of Formula II at low temperature in the presence of collidine.

11. The method of claim 10, wherein cleavage of the pivalate ester of the compound of Formula IIb is effectuated using NaOMe in MeOH with subsequent cyclization to form a compound of Formula IIc.

12. The method of claim 9, wherein said compound of Formula IIc is oxidized to form a diastereomeric mixture of sulfoxides to eliminated a sulfinic acid.

13. The method of claim 9, wherein:

$R^1$ is a member selected from the group consisting of optionally substituted $C_1$–$C_6$ alkyl, and optionally substituted $C_5$–$C_6$ cycloalkyl;

$R^2$ is a hydrogen; and $R^4$ is a member selected from the group consisting of halogen, and $S(O)_n$—$R^6$, wherein $R^6$ is an optionally substituted alkyl, wherein n is 1 or 2.

14. The method of claim 13, wherein:

$R^1$ is $C_1$–$C_6$ alkyl;

$R^2$ is a hydrogen;

$R^4$ is a halogen, wherein n is 1 or 2.

15. The method of claim 14, wherein:

$R^1$ is a member selected from the group consisting of methyl, ethyl, propyl and butyl.

16. The method of claim 9, wherein said compound of Formula II has the formula:

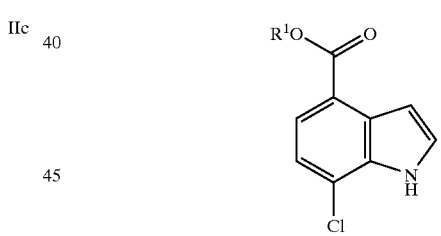

IIe wherein $R^1$ is a member selected from the group consisting of methyl, ethyl, propyl and butyl.

17. The method of claim 16, wherein: $R^1$ is methyl.

* * * * *